United States Patent [19]

Brandes et al.

[11] Patent Number: 4,803,214

[45] Date of Patent: Feb. 7, 1989

[54] FUNGICIDAL ACTIVE COMPOUND COMBINATIONS

[75] Inventors: Wilhelm Brandes, Leichlingen; Paul Reinecke, Leverkusen; Helmut Kaspers, Leverkusen; Hans Scheinpflug, Leverkusen; Jörg Stetter, Wuppertal, all of Fed. Rep. of Germany

[73] Assignee: Bayer Aktiengesellschaft, Leverkusen, Fed. Rep. of Germany

[21] Appl. No.: 144,822

[22] Filed: Jan. 15, 1988

[30] Foreign Application Priority Data

Jan. 22, 1987 [DE] Fed. Rep. of Germany ....... 3701715

[51] Int. Cl.$^4$ ..................... A01N 41/02; A01N 43/64
[52] U.S. Cl. ...................................... 514/383; 514/600
[58] Field of Search ................................ 514/383, 600

[56] References Cited

U.S. PATENT DOCUMENTS 3,341,403  9/1967  Klauke .................. 514/600

FOREIGN PATENT DOCUMENTS 0076370  4/1983  European Pat. Off. .

Primary Examiner—Allen J. Robinson
Attorney, Agent, or Firm—Sprung, Horn, Kramer & Woods

[57] ABSTRACT

A fungicidal composition comprising

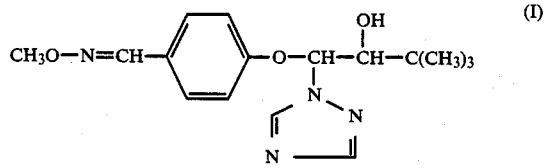

and at least one of

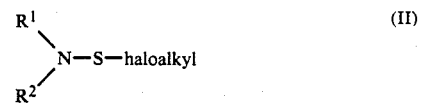

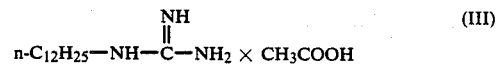

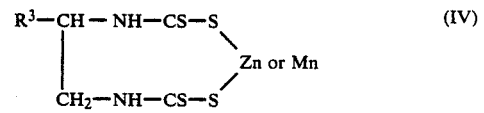

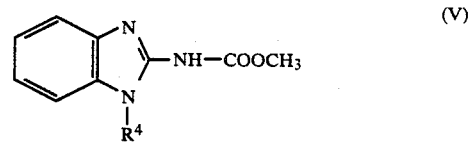

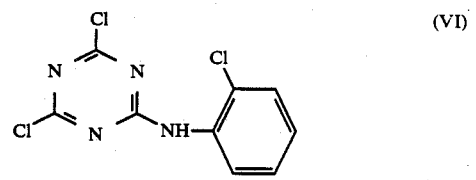

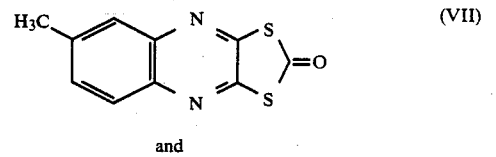

and

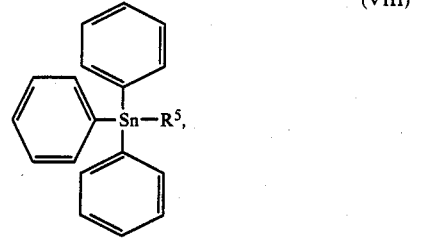

2 Claims, No Drawings

FUNGICIDAL ACTIVE COMPOUND COMBINATIONS

The present application relates to new active compound combinations which comprise, on the one hand, known 3,3-dimethyl-1-(4-methoximinomethylphenoxy)-1-(1,2,4-triazol-1-yl)-butan-2-ol and, on the other hand, further known fungicidal active compounds, and are very highly suitable for combating phytopathogenic fungi.

It has already been disclosed that 3,3-dimethyl-1-(4-methoximinomethyl-phenoxy)-1-)1,2,4-triazol-1-yl)butane-2-ol has a fungicidal potency (cf. EP-OS (European Published Specification) No. 0,076,370). The activity of this substance is good; however, in many cases it leaves something to be desired at low application rates.

It is furthermore already known that numerous azole derivatives, morpholine compounds and polyhalogenoalkylthio derivatives can be employed for combating fungi (cf. K. H. Büchel "Pflanzenschutz und Schädlingsbekämpfung" [Plant protection and combating of pests], pages 140, 141 and 146 to 153, Georg Thieme Verlag, Stuttgart 1977). However, the action of the substances concerned is not always satisfactory at low application rates.

It has now been found that the new active compound combinations of 3,3-dimethyl-1-(4-methoximinomethyl-phenoxy)-1-(1,2,4-triazol-1-yl)-butan-2-ol of the formula

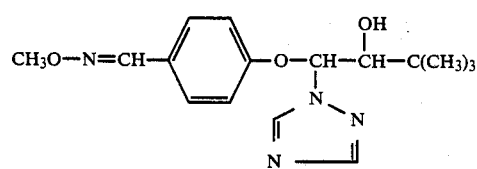
(I)

and (A) polyhalogenoalkylthio derivatives of the formula

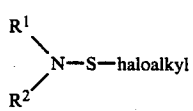
(II)

$R^1 = (CH_3)_2N-SO_2-$, (IIa)

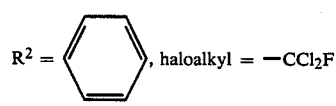, haloalkyl = $-CCl_2F$ (DICHLOROFLUANID)

$R^1 = (CH_3)_2-N-SO_2-$, $R^2 =$ 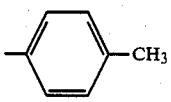—CH₃ (IIb)

haloalkyl = $CCl_2F$ (TOLYFLUANID)

$R^1$ together with $R^2 =$ 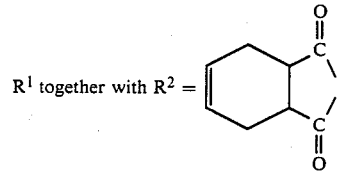 (IIc)

haloalkyl = $CCl_3$ (CAPTAN)

and/or (B) a guanidine derivative of the formula

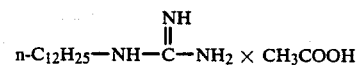
(III)

(DODINE)

and or (C) dithiocarbamates of the formula

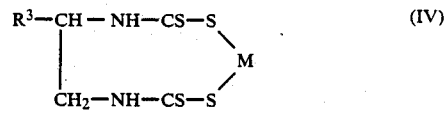
(IV)

$R^3 = H, M = Zn$ (ZINEB) (IVa)
$R^3 = H, M = Mn$ (MANEB) (IVb)
mixture of (IVa and IVb) (MANCOZEB) (IVc)
$R^3 = CH_3, M = Zn$ (PROPINEB) (IVd)
tris-[amine-zinc ethylene-bis-(dithiocarbamate)- (IVe)
polyethylene-bis-(thiuram disulphide)
(METIRAM-D)

and/or (D) benzimidazole derivatives of the formula

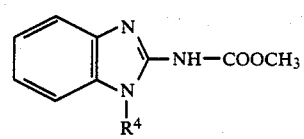
(V)

$R^4 = H$ (CARBENDAZIM) (Va)
$R^4 = -CO-NH-C_4H_9$ (BENOMYL) (Vb)

and/or (E) a triazine derivative of the formula

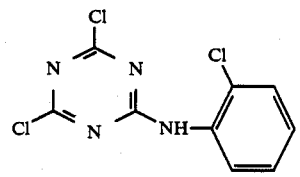
(VI)

(ANILAZINE)

and/or (F) a quinoxaline derivative of the formula

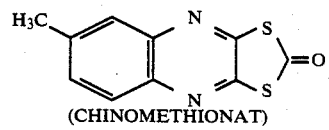
(VII)

(CHINOMETHIONAT)

and/or (G) an organotin compound of the formula

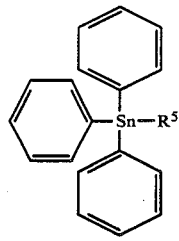

(VIII)

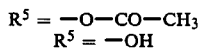

$R^5 = -O-CO-CH_3$ (VIIIa)
$R^5 = -OH$ (VIIIb)

have very good fungicidal properties.

Surprisingly, the fungicidal action of the active compound combinations according to the invention is significantly greater than the sum of the actions of the individual active compounds. An unforeseeable, true synergistic effect is therefore present and not only an addition of action.

Preferred active compound combinations according to the invention are mixtures which contain the active compound of the formula (I) and compounds of the formulae (II), (III), (IVc), (IVd), (IVe), (V), (VI) or (VIII).

Particularly preferred active compound combinations according to the invention are mixtures which contain the active compound of the formula (I) and
dichlofluanid of the formula (IIa) or
tolylfluanid of the formula (IIb) or
dodine of the formula (III) or
mancozeb of the formula (IVc) or
propineb of the formula (IVd) or
metiram D of the formula (IVe) or
carbendazim of the formula (Va) or
benomyl of the formula (Vb) or
anilazine of the formula (VI).

From the structural formula for the active compound of the formula (I), it can be seen that the compound has two asymmetrically substituted carbon atoms. Further, the oximether grouping may exist in a syn- and an anti-form. The product can therefore exist as a mixture of different isomers or alternatively in the form of a single component. The active compound of the formula (I) is known (cf. EP-OS (European Published Specification) No. 0,076,370).

The fungicidal active compounds additionally present in the combinations according to the invention are likewise known. The active compounds are described in detail in the following publications:

(A): R. Wegler, "Chemie der Pflanzenschutz- und Schädlingsbekämpfungsmittel" [Chemistry of plant protection agents and pesticides], volume 2, pages 95 and 108 to 110, Springer Verlag Berlin/Heidelberg-/New York, 1979;

(B): R. Wegler, loc. cit., page 70;

(C): R. Wegler, loc. cit., pages 65 and 66 and K. H. Büchel, "Pflanzenschutz und Schädlingsbekämpfung", [Plant protection and combating of pests], pages 136 and 137, Georg Thieme Verlag, Stuttgart 1977;

(D): DE-AS (German Published Specification) No. 1,209,799, DE-OS (German Published Specification) No. 1,932,297, U.S. Pat. No. 3,010,968 and K. H. Büchel, loc. cit., page 152;

(E): R. Wegler, loc. cit., page 120;

(F): R. Wegler, loc. cit., page 128 and (G): K.H. Buchel, loc. cit., page 125.

The active compound combinations according to the invention contain, besides the active compound of the formula (I), at least one active compound from the compounds of groups (A) to (G). In addition, they may also contain further fungicidally active admixed components.

The synergistic effect becomes particularly clear when the active compounds are present in the active compound combinations according to the invention in certain weight ratios. However, the weight ratios of the active compounds in the active compound combinations can be varied within a relatively wide range. In general, 0.5 to 100 parts by weight, preferably 2 to 20 parts by weight, of active compound from group (A), 0.5 to 50 parts by weight, preferably 2 to 20 parts by weight, of active compound from group (B), 0.5 to 100 parts by weight, preferably 5 to 100 parts by weight, of active compound from group (C), 0.5 to 20 parts by weight, preferably 0.5 to 10 parts by weight, of active compound from group (D), 1 to 100 parts by weight, preferably 5 to 50 parts by weight, of active compound from group (E), 0.5 to 20 parts by weight, preferably 0.5 to 10 parts by weight, of active compound from group (F), 1 to 100 parts by weight, preferably 2 to 50 parts by weight, of active compound from group (G), are present per part by weight of active compound of the formula (I).

The active compound combinations according to the invention have very good fungicidal properties and can be employed for combating phytopathogenic fungi, such as Plasmodiophoromycetes, Oomycetes, Chytridiomycetes, Zygomycetes, Ascomycetes, Basidiomycetes, Deuteromycetes etc.

The good toleration, by plants, of the active compound combinations at the concentrations required for combating plant diseases permits treatment of above-ground parts of plants, vegetative propagation stock and seeds, and of the soil.

The active compound combinations according to the invention have a very broad range of action and can be used against parasitic fungi which infest above-ground parts of plants or which attack the plants from the soil, and also against pathogens which can be transferred to the seed. Such active compound combinations have particular practical importance as seed dressings against phytopathogenic fungi which are transferred with the seed or occur in the soil and infest the crop plants from there. Seedling diseases, root rot, stem, halm, leaf, blossom, fruit and seed diseases, which are caused, in particular, by Tilletia, Urocystis, Ustilago, Septoria, Typhula, Rhynchosporium, Helminthosporium, Fusarium and Gibberella species. Through the systemic action of the one mixture partner, the plants are also often protected for a relatively long time after dressing against pathogens which are able to attack different parts of the seedling, for example true mildew fungi and rust fungi. In addition, the active compound combinations can also be employed as soil-treatment agents against phytopathogenic fungi and act against root rot and tracheomycoses, which are caused, for example, by pathogens of the genera Pythium, Verticillium, Phialophora, Rhizoctonia, Fusarium, Gibberella and Thielaviopsis.

However, when applied directly to the above-ground parts of plants, the active compound combinations according to the invention also exhibit an excellent action against pathogens on various crop plants, such as Oomycetes (Phytophthora, Plasmopora and Peronospora species), true mildew fungi (Erysiphe, Uncinula, Sphaerotheca and Podosphaera species and Leveillula taurica), rust fungi, Venturia species, Mycosphaerella species, Cercospora species, Alternaria species, Botrytis species, Fusarium species, Pyrenophora species, Cochliobolus species, Septoria species, Pseudocercosporella herpotrichoides, Pyricularia oryzae and Pellicularia sasakii.

The active compound combinations can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules of latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention can be present in the formations as a mixture with other known active compounds, such as fungicides, insecticides, acaricides and herbicides, as well as in mixtures with fertilizers.

The active compound combinations can be used as such or in the form of their formulations or the use forms prepared therefrom, such as ready-to-use solutions, emulsifiable concentrates, emulsions, suspensions, wettable powders, soluble powder, and granules. They are used in the customary manner, for example by watering, spraying, atomizing, scattering, brushing on, dry dressing, moist dressing, wet dressing, slurry dressing or encrusting.

In the tretment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The good fungicidal action of the active compound combinations according to the invention can be seen from the following examples. Whereas the individual active compounds have weaknesses in the fungicidal action, the combinations exhibit an action which extends beyond a simple addition of action.

A synergistic effect in fungicides is always present when the fungicidal action of the active compound combinations is greater than the sum of the actions of the individually applied action compounds.

The action to be expected for a given combination of two active compounds can be calculated as follows (cf. Colby, S. R., "Calculating synergistic and antagonistic responses of herbicide combinations", Weeds 15, pages 20–22, 1967): When X denotes the disease infestation, expressed in % of the untreated control, when active compound A is used in a concentration of m ppm, Y denotes the disease infestation, expressed in % of the untreated control, when active compound B is used in a concentration of n ppm, and E denotes the disease infestation expected, expressed in % of the untreated control, whe active compounds A and B are used in concentrations of m and n ppm, then $$E = \frac{X \times Y}{100}$$

If the actual fungicidal action is greater than calculated, the combination is superadditive in its action, i.e. a synergistic effect is present. In this case, the infestation actually observed must be less than the value calculated from the formula above for the expected infestation (E).

From the tables of the following examples, it can clearly be seen that the action found for the active compound combinations according to the invention is greater than the calculated value, i.e. a synergistic effect is present.

EXAMPLE A

Venturia test (apple)/protective solvent: 4.7 parts by weight of acetone
emulsifier: 0.3 parts by weight of alkyl-aryl polyglycol ether To produce a suitable preparation of the active compound, either 1 part by weight of active compound or active compound combination is mixed with the stated amounts of solvent and emulsifier, and the concentrate is diluted with water to the concentration desired, or a commercially available concentrate of active compound or active compound combination is diluted with water to the concentration desired in each case.

To test for protective activity, young plants are sprayed with the respective preparation of active compound (individual active compounds or active compound combinations) until dripping wet. After the spray coating has dried, the plants are inoculated with an aqueous conidia suspension of the apple scab pathogen (*Venturia inaequalis*) and then remain in an incubation cabin at 20° C. and 100% relative atmospheric humidity for one day.

The plants are then placed in a greenhouse at 20° C. and a relative atmospheric humidity of about 70%.

Evaluation is carried out 12 days after inoculation.

The active compounds, active compound concentrations and experimental result can be seen from the following tables.

TABLE A

| Venturia test (apple)/protective | | |
|---|---|---|
| Active compounds | Active compound concentration in the spray liquid in ppm | Disease infestation in % of the untreated control |
| — (control) | — | = 100 |
| (I) diastereomeric mixture | 0.05 | 63 |
| (IVc) | 0.85 | 68 |
| | | found / calculated* |
| (I) diastereomeric mixture + (IVc) | 0.05 + 0.85 | 15 / 43 |
| — (control) | — | 80 |
| (I) diastereomeric mixture | 0.125 | 65 |
| (IIa) | 1.25 | 61 |
| | | found / calculated* |
| (I) diastereomeric mixture + (IIa) | 0.125 + 1.25 | 12.5 / 40 |

*Calculated from the formula given on page 12.

EXAMPLE B

Botrytis test (bean)/protective solvent: 4.7 parts by weight of acetone
emulsifier: 0.3 parts by weight of alkyl-aryl polyglycol ether.

To produce a suitable preparation of the active compound, either 1 part by weight of the active compound or active compound combination is mixed with the stated amounts of solvent and emulsifier, and the concentrate is diluted with water to the desired concentration, or a commercially available concentrate of the active compound or active compound combination is diluted with water to the concentration desired in each case.

To test for protective activity, young plants are sprayed with the respective preparation of active compound (individual active compounds or active compound combinations) until dripping wet. After the spray coating has dried, 2 small pieces of agar covered with *Botrytis cinerea* are placed on each leaf. The inoculated plants are placed in a darkened, humid chamber at 20° C. The size of the infected spots on the leaves is evaluated 3 days after inoculation.

The active compounds, active compound concentrations and experimental results can be seen from the following table.

TABLE B

| Botrytis test (bean)/protective | | |
|---|---|---|
| Active compounds | Active compound concentration in the spray liquid in ppm | Disease infestation in % of the untreated control |
| — (control) | — | = 100 |
| (I) diastereomeric mixture | 100 | 72 |
| (IIa) | 5 | 64 |
| | | found / calculated* |
| (I) diastereomeric mixture + (IIa) | 100 + 5 | 38 / 46 |

*Calculated from the formula given on page 12.

It will be understood that the specification and examples are illustrative but not limitative of the present invention and that other embodiments within the spirit and scope of the invention will suggest themselves to those skilled in the art.

We claim:

1. A fungicidal composition comprising a fungicidally effective amount of 3,3-dimethyl-1-(4-methoximinomethylphenoxy)-1-(1,2,4-triazol-1-yl)-butan-2-ol of the formula

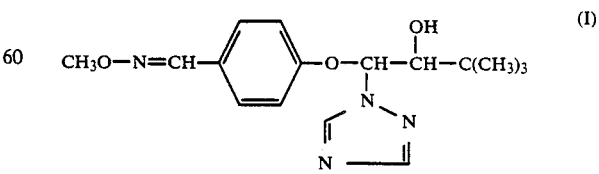

and at least one member selected from the group consisting of
a polyhalogenoalkylthio derivative of the formula $$R^1\diagdown N\text{—}S\text{—haloalkyl} \atop R^2\diagup \qquad (II)$$

wherein $R^1 = (CH_3)_n N-SO_2-$, $R^2 =$ 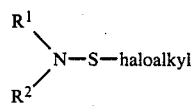, and haloalkyl $= -CCl_2F$ (DICHLOFLUANID) and (IIa)

-continued wherein $R^1 = (CH_3)_2-N-SO_2-$, $R^2 =$ ⟨p-tolyl⟩$-CH_3$ (IIb)

and haloalkyl $= CCl_2F$
(TOLYFLUANID).

wherein the ratio of I:II is 1:0.05 to 10 parts by weight.

2. A method of combating fungi which comprises applying to such fungi or to a fungus habitat a fungicidally effective amount of a composition according to claim 1.

* * * * *

UNITED STATES PATENT AND TRADEMARK OFFICE
CERTIFICATE OF CORRECTION

PATENT NO. : 4,803,214

DATED : February 7, 1989

INVENTOR(S) : Wilhelm Brandes et al

It is certified that error appears in the above-identified patent and that said Letters Patent is hereby corrected as shown below:

Col. 6, line 24      Correct spelling of --treatment--

Col. 7, line 68 and Col. 8, line 45      Delete "*Calculated from the formula given on page 12." and substitute --*Calculated from the formula given at Col. 6, line 64--

Signed and Sealed this

Thirteenth Day of February, 1990

Attest:

JEFFREY M. SAMUELS

*Attesting Officer*      *Acting Commissioner of Patents and Trademarks*